United States Patent [19]

Volkmann et al.

[11] Patent Number: 5,373,741

[45] Date of Patent: Dec. 20, 1994

[54] ULTRASONIC MEASURING DEVICE, ESPECIALLY SUITED TO NON-DESTRUCTIVE TESTING OF MATERIALS

[75] Inventors: Klaus Volkmann, Bergisch-Gladbach; Horst Pollok, Wesseling; Manfred Kickartz, Brühl, all of Germany

[73] Assignee: Krautkramer GmbH & Co., Hurth-Efferen, Germany

[21] Appl. No.: 81,987

[22] Filed: Jun. 24, 1993

[30] Foreign Application Priority Data

Jun. 27, 1992 [DE] Germany .................. 4221220

[51] Int. Cl.⁵ .............................................. G01N 29/00
[52] U.S. Cl. ........................................ 73/602; 73/620;
73/629; 330/60; 330/252
[58] Field of Search .............. 73/602, 1 DV, 620, 629,
73/631, 900, 626; 330/60, 252, 254

[56] References Cited

U.S. PATENT DOCUMENTS

| | | | |
|---|---|---|---|
| 4,205,555 | 6/1980 | Hashiguchi | 73/626 |
| 4,445,379 | 5/1984 | Yamaguchi et al. | 73/631 |
| 4,454,884 | 6/1984 | Seader | 73/631 |
| 4,763,525 | 8/1988 | Cobb | 73/599 |

*Primary Examiner*—Hezron E. Williams
*Assistant Examiner*—Helen C. Kwok
*Attorney, Agent, or Firm*—K. S. Cornaby

[57] ABSTRACT

An ultrasonic measuring device that is especially suited to nondestructive testing of materials is fitted with an ultrasound test head 72, a transmitter (74) and a receiver (76) that is characterized by a broadband logarithmic amplifier (78). This amplifier consists of several amplifier stages that are identical in construction and connected in series. Each amplification stage is characterized by the fact that it contains two transistorized individual amplifiers, namely a first and a second differential amplifier that are connected to one another and whose transistors (20, 22; 24, 26) are each interconnected at their base and at their collector. Each of these transmitters is connected at the emitters via inverse feedback resistors (34, 36; 40, 42) to a constant-current source (46, 50). At least the constant-current source 46 of one of the two differential amplifiers of an amplification stage is connected on one side to a digital analog transformer (58) that provides corrections for calibrating each connected constant-current source (46).

15 Claims, 3 Drawing Sheets

ULTRASONIC MEASURING DEVICE, ESPECIALLY SUITED TO NON-DESTRUCTIVE TESTING OF MATERIALS

BACKGROUND OF THE INVENTION

The invention pertains to an ultrasonic measuring device that is especially suited to non-destructive testing of materials. It is fitted with an ultrasound test head, a transmitter and a receiver. A broad-band logarithmic amplifier that is built up of several amplifier stages which are identical in construction and which are connected in series is incorporated in the head.

Ultrasonic measuring devices that function according to the impulse echo process employ amplifiers that have a pitch range value for amplification of around $10^5$ (100 dB). In linear amplifiers the echo display on the monitor is proportional to the input voltage of the echo signal at the ultrasonic head. In a logarithmic amplifier the displayed echo height is proportional to the logarithm of the voltage in the test head. The logarithmic amplifier possesses in comparison to the linear amplifier a significantly greater dynamic range (relationship of the greatest to the smallest signal that can be detected on the monitor). Disadvantageous is however the required resolution of the maximum amplitude and the distortion of the signal type. These result from the amplified dynamic range.

Ultrasonic measuring devices of the type noted above in the introduction are familiar from the DE book by J. and H. Krautkrämer: "Testing Materials by Means of Ultrasound," 4th. Ed., published by Springer. The increasing use in modern ultrasound testing systems of computer controlled amplifiers enables electronically regulated amplifiers to be employed more and more. It is advantageous if the adjustable amplifier can be switched between linear and logarithmic function. A choice can then be made between the large dynamic range that can be achieved.

In the ultrasonic measuring devices that are already familiar, the logarithmic amplifier is composed of five individual high-frequency amplifiers that are of identical construction and connected in series. For each individual amplifier stage the amplifying factor is the same, i.e., in a five-stage 100 dB amplifier the function for each is 20 dB. In addition, for all stages the saturation point at which the input (jumping-off) signal, in spite of increasing input voltage, remains constant, is also absolutely the same. By means of a video rectifier stage at the head of this chain, as well as behind each amplifier stage, a video signal is shunted off and directed to an adding stage.

In actual practice such a logarithmic amplifier is difficult to construct. Especially problematic is the requirement that all amplifier stages demonstrate the required identical qualities.

The data sheet concerning the Plessey integrated amplifier SL 531 C offers another way to construct a logarithmic amplifier from a series of individual, similar amplifier stages. This sheet describes a non-symmetric differential amplifier stage with two differential amplifiers. In a specific example a logarithmic amplifier is achieved by linking six such amplifiers in series. In this example, the logarithmic signal appears only at the head of the chain, and an adding stage is not required. Each of the differential amplifiers at any one amplifier has its own source for constant current, both the current sources being adjustable externally. It is not possible to regulate individually a single constant-current source in the integrated amplifier.

Even in this logarithmic amplifier two problems result from variations in the characteristics of the individual amplifier stages which are arranged in series. In actual practice it is not possible to ensure that all amplifier stages possess identical characteristics to a sufficient degree. Thus, this kind of amplifier always has a characteristic that to a greater or lesser degree detracts from the desired logarithmic function.

It is the purpose of the invention to further develop the ultrasonic measuring device so that the logarithmic amplifier can be regulated in such a way that, over a long period of time, its curve diverges as minimally as possible from a logarithmic amplifier curve.

SUMMARY OF THE INVENTION

This goal was achieved as follows. Proceeding from the ultrasonic measuring devices of the kind noted initially, each amplifier stage is characterized by two transistorized individual amplifiers, namely a first and a second differential amplifier. The two are integrated into each other, and their transistors are in each instance linked together at their bases and at their collector. The emitters are connected via inverse feedback resistances to a constant-current source. In addition, at least the constant-current source of one of the two differential amplifiers of an amplifier stage is connected on the input side to a digital analog transformer. This transformer is connected to a data processing unit that provides correcting data for the calibration of each attached constant-current source.

This amplifier for an ultrasonic measuring device functions in accordance with the principle of the integrated amplifier stages manufactured by Plessey. The characteristic curve for amplification of each individual amplifier stage has two ranges. When the input signal is small the amplifier stage has an amplifying function that is greater than 1, e.g. 10 dB; when the input signal is greater the amplification is 1. Thus the characteristic amplification curve has a "break" or sharp change in the curve, and for this reason amplifier stages of this kind are frequently designated "break" amplifiers. By arranging in series a sufficient number of such amplifier stages it is possible to achieve the desired logarithmic characteristic amplification curve of the amplifier.

The invention further aims to ensure that at least one of the two constant-current sources of each individual amplifier stage of the various amplifier stages that are connected in series can be adjusted individually. In this way it is possible to compensate for differences in the individual amplifier stages and tune the individual amplifier stages to essentially identical characteristic curves. This tuning can be effected at any desired or particular time, which is to say whenever the user desires this or whenever a significant deviation from the desired characteristic curve is registered.

In this way the invention makes it possible for the first time to individually adjust and render as similar as possible the amplifier stages that are constructed identically and linked together in series in a chain. Thus the desired logarithmic characteristic curve for amplification can be approximated to the best possible degree. But of special advantage is the fact that the maximum deviation from a purely logarithmic process can be entered into the device. Thus the user knows the maximum error that can occur for an ultrasonic measuring device that is fitted with the amplifier.

Individual adjustment of the constant-current source of an amplifier stage is possible by means of a digital analog transformer (herein designated as a "D/A transformer"). The D/A transformer receives the digital data from the data processing unit. A suitable program by means of which the individual amplifier stages are rendered as similar as possible is entered in the data processing unit. The data processing unit is in its turn controlled by input signals which it receives from a calibration unit. This calibration unit can be linked on the one hand to the input and on the other to the output of the amplifier from the amplifier stages that are linked in series, and it renders it possible to receive input signals of various amplitude and register in each instance the output signals that were received. Positional values can be derived from the discrepancy between the output signals and the expected value for an exactly logarithmic characteristic curve. These positional values are processed in the data processing unit to provide items of information that are directed to the individual D/A transformers.

Because adjustment of any one individual amplifier stage affects the other amplifier stages, all amplifier stages must be considered when the device is being adjusted. If the amplifier is characterized by "n" amplifier stages, then the data processing unit must compensate for and adjust n amplifier stages in such a way that the optimal result is achieved, namely a logarithmic curve that, as far as possible, approximates to a logarithmic amplifier curve. Ideally, the data processing unit should be running a convergence program that makes it possible to harmonize all n adjustment procedures in such a way that, in the end, the optimal result is achieved. Yet even without such a divergence program the ultrasonic measuring device that is constructed in accord with the invention makes it possible to minimalize the divergences of each individual amplifier stage from the given theoretical values. In this way optimal approximation to the logarithmic amplifier curve is not achieved, but the maximum divergence from the logarithmic amplifier curve is nevertheless known.

One especially advantageous further development of the amplifier constructed in accordance with the invention consists in the possibility of fitting it for linear amplification. This is achieved by adjusting the constant-current sources in such a way that the "break" point either occurs at 0, in which case the whole amplifier stage has an amplification factor of 1; or it lies in the range of the saturation point for the amplifier stage, in which case the whole amplifier stage has a pregiven amplification Vo. Because each individual amplifier stage in the chain that consists of n amplifier stages can be adjusted to the one or the other amplification factor, the total of the amplification for the linear amplifier can be set between 1 and Vo.

For general information on differential amplifiers the reader is referred to the DE book "Semiconductor Technology" by Tietze and Schenk, 5th. Ed., published by Springer Publishers.

The total linear amplification of several differential amplifier stages arranged in series in accordance with the invention is varied by modifying one or several differential amplifier stages between the values $V=1$ and $V=Vo$. If all differential amplifier stages are set so that $V=Vo$ then the amplifier is operating at maximum amplification, namely: $Vges=Vo^n$, n being the number of differential amplifier stages that are arranged one behind the other. The least amount of amplification is achieved when all n-differential amplifier stages are switched so that $V=1$, in which case the total amplification is also 1. Between these ranges the amplification totals Vges can be adjusted with the values Vo, $Vo^2$, $Vo^3$.... If for example the value 10 dB is selected for Vo, and if $n=8$ is selected for the (amplifier) stage, then the total amplification can be adjusted in increments of 10 between 0 and 80 dB.

On switching during linear operation between two different amplification factors no jump in voltage occurs at the outlet point of the differential amplifier stage. This characterizes one of the advantages of the arrangement that is in accordance with the invention. In linear operation the third constant-current source with the current value I2 is not used. In order to switch between the amplification $V=1$ and the amplification $V=Vo$ the second constant-current source with the current value half-I1 is switched by means of an alternating switch either parallel to the first current source of the same value half-I1, in which ease the second differential amplifier in the differential amplifier stage is at earth potential; or it is switched to the input point of the second differential amplifier, in which case both differential amplifiers in the differential amplifier stage are active. In this way the total current is in each case I1, so that on switching the collector resistance of each branch that is common to all no change in voltage occurs.

BRIEF DESCRIPTION OF THE DRAWINGS

Further advantages and characteristics of the invention result from the remaining claims sought and from the following description of three illustrative examples of the invention. These examples in no way limit the patents sought and are explained in greater detail with reference to the drawing. Of these:

DETAILED DESCRIPTION OF THE DRAWING

Figure 1:
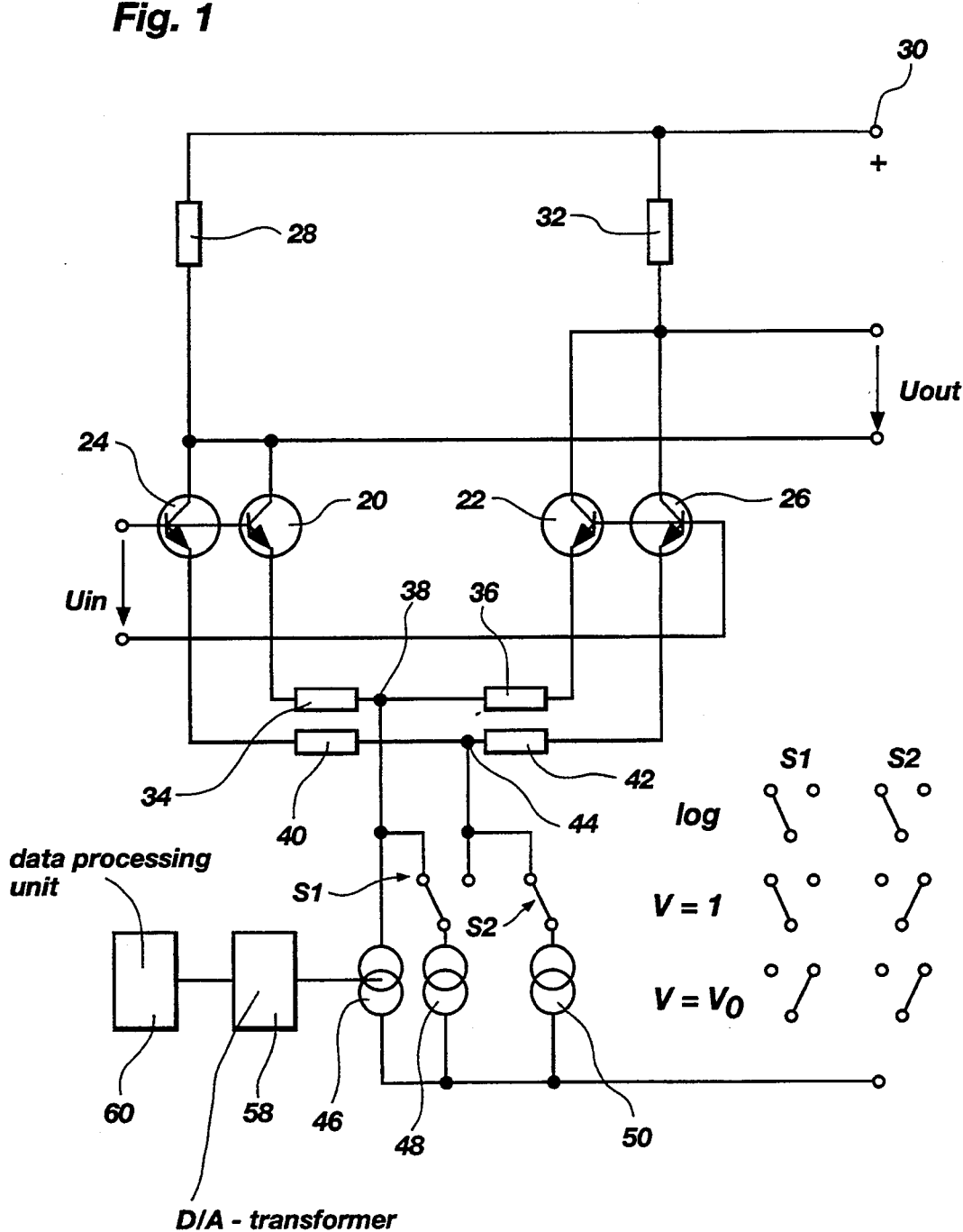
FIG. 1 shows the circuit diagram for a differential amplifier stage with two differential amplifiers integrated into each other.

The amplifier stage evident from FIG. 1 is fitted with transistors and constructed symmetrically. It consists of a first differential amplifier with the two transistors 20, 22: in what follows these are designated the inner transistors by reason of their arrangement. The amplifier stage is also fitted with a second differential amplifier with two transistors 24, 26: in what follows they are designated external transistors. The two left transistors 20, 24 and also the two right transistors 24, 26 are linked together at their bases as well as at their collector. An input voltage Uin is situated on the one side between the two bases of the two left transistors 20, 24 that are linked together, and on the other side it is sited between the two bases 22, 26 of the transistors on the right that are linked together. Both collectors of the transistors 20, 24 that are positioned on the left-hand side are connected via a collector resistance 28 to the + pole of a voltage source 30. The same is true for the two collectors that are linked together from the transistors on the right 22, 26: they are connected via a collector resistance 32 to the voltage source 30. The resistance values of the two collector resistances 28, 32 are identical.

The emitters on the two inner transistors 20, 22 are each connected to an inverse feedback resistance 34, 36 with a first point 38, and in the same way the two emitters on the external transistors 24, 26 are each connected via an inverse feedback resistance 40, 42 to a second input point 44.

The first input point 38 is permanently connected with an initial, adjustable constant-current source 46 that in normal operation provides the current. In addition, both the input points 38, 44 can be connected via an arrangement of switches S1, S2 to two further constant-current sources 48, 50 that can not be adjusted. Reference to this circuit will be made below. It consists of a double-throw switch S1 (on the left in FIG. 1) and an in-switch S2 (shown on the right in FIG. 1). These can occupy three different configurations or respectively switch positions, which are shown at the bottom right of FIG. 1. The second constant-current source 48 supplies the current I1/2, which corresponds exactly to the current provided by the first constant-voltage source 46. The third constant-voltage source 50 supplies the current I2. In the concrete example the switches are constructed as electronic switches.

In the complete circuitry constructed in accord with FIG. 1 the switch position "logarithmic" is displayed. This is shown on the upper right in the three switch positions that are arranged one above the other. In this position the second constant-current source 48 is switched parallel to the first constant-current source 46 so that the current I1 is introduced into the first input point 38. The third constant-current source 50 is connected to the second input point 44 so that the current I2 can be supplied at this point.

In switch position $V=1$, that is to say when the total amplification of the illustrated differential amplifier stage is equal to one, both the inner transistors 20, 22, which constitute the first differential amplifier, are operated as for a logarithmic switch position. Thus, the total current I1, which is derived from the two constant-current sources 46, 48 that are switched in parallel, is introduced into the first input point 38. In this case however the second differential amplifier from the two external transistors 24, 26 is at earth potential.

In switch position $V=Vo$ also the third constant-current source 50 is not required. The current I1/2 is introduced in each instance into both the first input point 38 and the second input point 44 via the first constant-current source 46 or respectively via the second constant-current source 48.

The resistance values of the two collector resistances 28, 32, which are equal in size, are approximately as large as the resistance values of the two effective inverse feedback resistances 34, 36. These two are equal in size so that the first differential amplifier, consisting of the two inner transistors 20, 22, has the amplification factor $V=1$.

The two effective inverse feedback resistances 40, 42 of the two external transistors 24, 26 are also the same size, but their resistance value is significantly smaller than that of the same-sized resistors 28, 32, 34, 36. Because of this fact the second differential amplifier, which consists of both the external transistors 24, 26, has an amplification with the amplification factor $V=Vo-1$.

An output voltage Uout occurs between the two collectors of the transistors on the left side 20, 24, which are linked together, and the two collectors of the transistors which are situated on the fight hand side 22, 26. The current value I2 provided by the third constant-current source 50 is smaller than the value of the current provided by the two constant-current sources 46, 48 which are equal in size. Its value is $I2<I1/2$.

For small input voltages Uin both differential amplifiers function when switching is in the logarithmic position. The total amplification results as a quotient from the collector resistance 28 or 32 to the parallel switching from each of the effective inverse feedback resistances of each differential amplifier, that is to say for example the inverse feedback resistances 42, 40. With input voltages Uin that are greater than I2 times the value of an inverse feedback resistance 40 or 42 of the external transistors 24, 26, the differential amplifier consisting of the two external transistors 24, 26 is overridden. Above this value for input voltage Uo only the two internal transistors 20, 22 of the first differential amplifier function. Expressed in other words, the total amplification is determined only by the relationship of a collector resistance 28 or 32, to the inverse feedback resistance 40 or 42. This value is 1. Above the stated limit the amplification is therefore to be sought where $V=1$.

Figure 2:
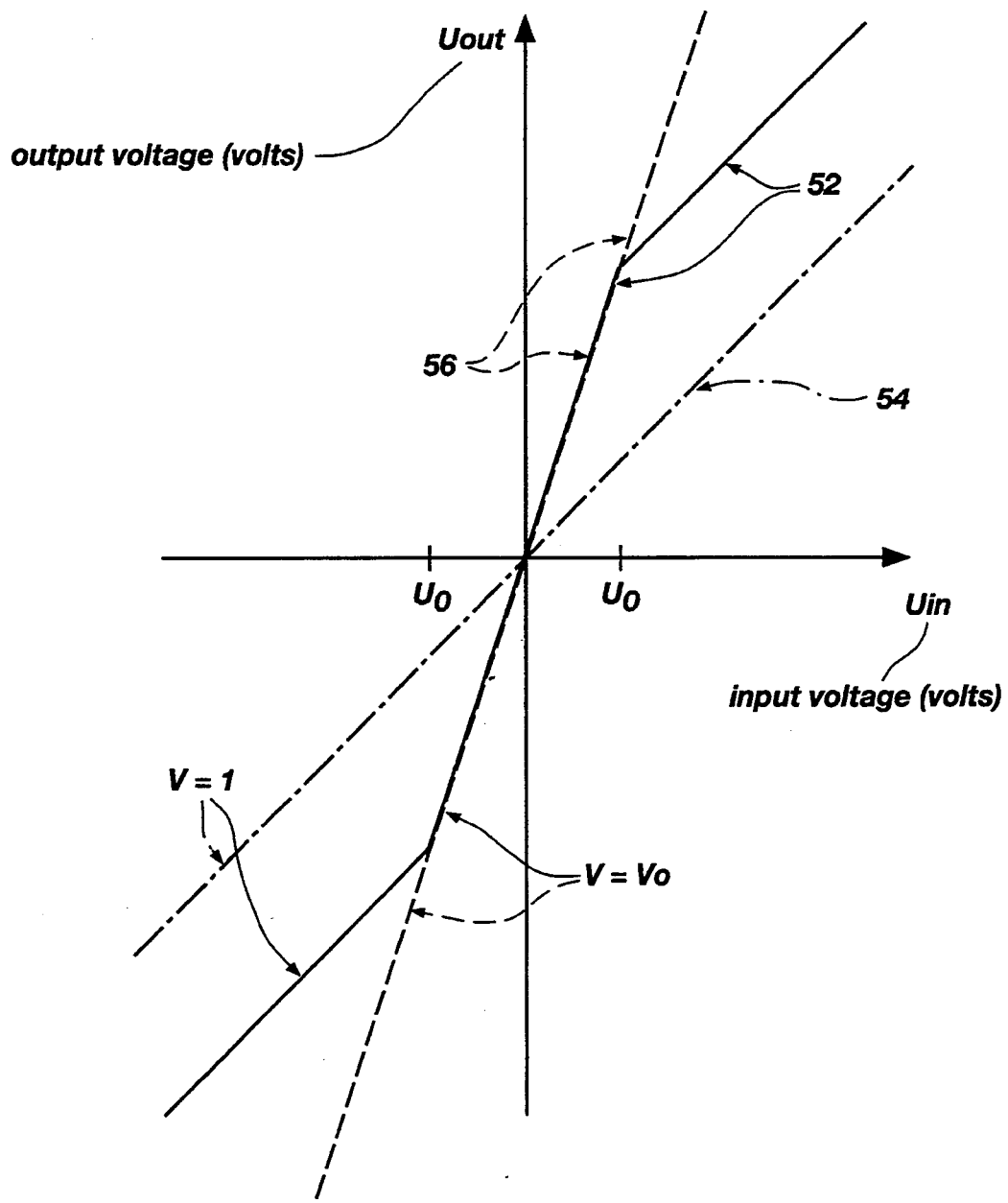
FIG. 2 shows a representation of the characteristic curve Uout over Uin for the three switching positions for a differential amplifier.

These relationships are demonstrated in FIG. 2 in the drawn-out polygon feature 52. For input voltages Uin in the range ±Uo, which is the above noted threshold for the input voltage, it has the pitch $V=Vo$, and for an input voltage Uin that in its absolute value is above Uo it has the pitch $V=1$.

When switching position is $V=1$, that is to say when total amplification is 1, both the external transistors 24, 26 are at earth potential, and only the first differential amplifier consisting of the two inner transistors 20, 22 is functioning. A straight line 54 with the pitch $V=1$ results as shown in FIG. 2. This straight line is represented by a dash-dot.

In the switching position $V=Vo$ such a high current I1/2 from the constant-current source 48 is introduced into the second input point 44 that the resulting threshold value for the input voltage Uin is significantly greater than Uo. This second threshold lies at I1/2 times the value of an inverse feedback resistance 40, 42. In consequence, the differential amplifier consisting of the two external transistors 24, 26 is not overridden within the projected range of operation, that is, the permissible input voltage Uin. As a result, the differential amplifier stage now has throughout a total amplification $V=Vo$, as is shown in FIG. 2 in the broken lines 56. This overlaps in part with the characteristic curve 52 for the logarithmic situation.

Switching position S1 and S2 is deliberately selected so that, on switching, a new contact is first established before the old contact is interrupted. This guarantees that, when switching from the first differential amplifier to the second differential amplifier by means of S1 of the constant-current source 48, the situation does not arise where both input points 38, 44 are for a brief instant not connected to constant-current source 48. This ensures that, when switching between $V=1$ and $V=Vo$, the total current I1 is constantly flowing in both the two collector resistances 28, 32 so that no jump/break in voltage occurs.

A second switching configuration which is in accord with the invention but which is not shown in FIG. 1 is also possible. In it, each individual differential amplifier does not have a common input point; rather, the constant-current source is in each instance applied directly to the emitter. Thus two constant-current sources are required for each individual differential amplifier. In this instance it is no longer necessary to provide two individual inverse feedback resistances; one inverse feedback resistance with the value derived from the switching series of the pertinent inverse feedback resistance suffices. Thus not three but six constant-current sources are required. As is shown in FIG. 1, three current sources are connected to the two left emitters. In accord with the arrangement shown in FIG. 1, a corresponding arrangement is provided for the three constant-current sources which are connected via a similarly constructed switching arrangement to the two emitters on the right-hand side. In such a configuration only the one inverse feedback resistance is at earth potential when at rest. Thus the total amplification too is adjustable by varying the inverse feedback resistance without a change to the output voltage Uout.

The adjustable constant-current source 46 is connected on its input side to the output of a D/A transformer 58. This in its turn is connected with its digital input to the output of a data processing unit 60. When the unit is in logarithmic mode, but also when it is being operated linearly, it is possible to calibrate the amplification stage by adjusting the constant-current source 46; that is, it is possible to adjust it to its desired value. This is of decided advantage when operating in the logarithmic mode, because in that form of operation all the individual amplification stages can be adjusted to achieve the best possible approximation to a logarithmic amplification curve; but advantages also result when operating in the linear mode because the total linear amplification can be predicted more precisely.

It is possible to make adjustable not only the constant-current source 46 but also the other constant-current sources. It is also possible to make the constant-current source 46 adjustable over such a wide range that the second constant-current source 48 can be totally eliminated. In that case only two constant-current sources are required for each amplification stage, and adjustment of the constant-current sources 46 via the data processing unit 60 is employed. With purely logarithmic amplifiers the second constant-current source 48 is not necessary if the constant-current source 46 is adjustable within the range around I1.

Figure 3:
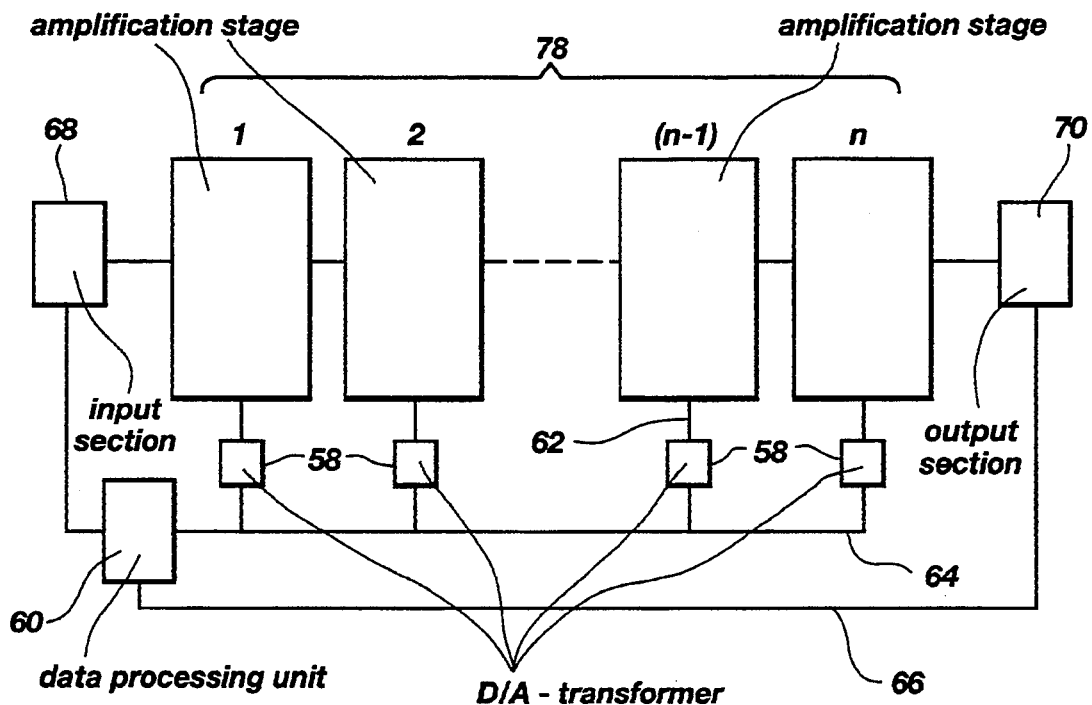
FIG. 3 shows a block circuit diagram for an amplifier with n amplifier stages, a data processing unit and a calibration component.

FIG. 3 shows in the plan of a block switching diagram a complete amplifier that is constructed of the amplification stages that are constructed in accord with FIG. 1 and FIG. 2. The amplifier has a total of n such amplification stages as are here indicated by the reference numbers 1, 2 . . . (n−1), n. A constant-current source 46 that is adjustable is sited in each individual amplification stage. In each instance it is attached via a connection 62 to a D/A transformer 58. The total n D/A transformers 58 are connected via a bus connection 64 to the data processing unit 60. This in its turn is connected to a calibration unit 66 that in essence is composed of an input section 68 and an output section 70. The input section produces voltages of various amplitudes that in each case are connected to the input of the amplifier, which is to say to the first amplification stage 1. The output section 70 measures for each individual input voltage the output signals that occur at the amplifier's output. The data processing unit derives from the discrepancy between the value of the output signals and the theoretical value that should have been recorded information as to how the individual constant-current sources 46 should be adjusted.

Calibration of the logarithmic amplifier can proceed according to an iterative process. Good results were achieved using a calibration process based on the Newton process.

For an n-stage amplifier the "break" voltages of each individual amplification stage 1, 2 . . . (n−1), n should lie in the range a dB. First, the nominal control current for a current I1 are set for all amplification stages. The input section 68 now produces step by step n test input signals with amplitudes in stages of a dB. These must lie within the definition range of the logarithmic characteristic curve. The pertinent output amplitudes are measured by means of the output component 70. Actual use has shown that it is practical to select the "broken" voltages $U_1 \ldots U_n$. The output levels that are measured will in general differ from the expected straight lines. By means of a linear transformation better values for the control currents I1 are determined from the variations.

This process is repeated as often as necessary until the variations that are measured are smaller than a given threshold for a tolerance.

In detail, the procedure works as follows: For a given logarithmic amplifier one expects an approximated linear connection between the logarithmic input levels $U_{dB}$ and the output signals $U_{out}^{target}$.

$$U_{out}^{target}(U_{dB}) = c_0 + c_1 * U_{dB} \quad (1)$$

in which $$U_{dB} = 20 * \log_{10}(U_E/U_o), \ U_o \leq U_E \leq n * U_o \quad (2)$$

signifies. The coefficients $c_o$ and $c_1$ result from the individual dimensioning of the amplifier.

The deviation of the measured output signals from the desired output characteristic in accord with equation (1) in dB is $$\delta F = \frac{U_{out}^{actual}(U_{dB}) - U_{out}^{target}(U_{dB})}{c_1} \quad (3)$$

In this, $U_{out}^{actual}(U_{dB})$ provides the actual relationship between the input signal in dB and the output voltage.

The task now is to find corrections for the n control currents $\delta I_{ST,j}$ (j=0 . . . n) from the n measured variations $\delta F_i$ (i=0 . . . n) so that the $\delta F$ subsequently become as small as possible. By reason of the mutual dependency between the amplification stages the general linear onset is selected:

$$\delta F^{(n)}_{new} = \delta F^{(n)}_{old} - D * \delta I^{(n)} \quad (4)$$

In this equation those quantities that are designated by $(n)$ are n-dimensional column vectors. The $\delta F^{(n)}$ contain the deviations from the expected dB-relationship at the n measuring points, $\delta I^{(n)}$ contains the corrections for the control currents of the n amplification stages. D is an n by n matrix the components of which are given by the partial deductions $$D_{ij} = \frac{d(\delta F)_i}{d(I)_j} \quad (5)$$

In order to convert δF (in linear approximation) in the next iteration step to 0, you must choose the control-current correction in accord with $$\delta I^{(n)} = D^{-1} * \delta F^{(n)} \quad (6)$$

In this equation $D^{-1}$ signifies the inverted matrix.

It is possible to select from two processes in order to determine the matrix D or respectively $D^{-1}$. You may measure the partial deductions for each individual switching position and they can be calculated theoretically for a typical switching.

The first process ensures the quickest convergence, but it requires a large number of measurements (72 per stage for an eight stage amplifier) and is susceptible to mistakes during measurement. For this reason the second process is selected. The matrix is derived from the results of a switching simulation with component parts that are free of tolerance. The inverted matrix is calculated once and for all. For this reason it is necessary to take only n measurements and complete a multiplication of a vector with a matrix.

Simulations show that it depends on the dimensions of the amplifier whether the conditions for convergence of the Newton-process are fulfilled. It is nevertheless possible to find dimensions that not only fulfil the requirements but also show a good convergence relationship.

The influence of measurement errors by reason of whistling when input levels are low poses a further problem. This can be countered by introducing weights. Equation (5) is then to be modified perhaps according to the formula $$D_{ij} = w_i * \frac{d(\delta F)_i}{d(I)_j} \quad (5')$$

$w_i$ being a characteristic weighting factor for the i-ten input level. For larger input signals $w_1$ is approximately 1, and for smaller input signals smaller $w_i$ values are to be selected. The convergence is slower for low levels. For this reason there is less distortion of the results for high levels. The weights can be determined theoretically or through actual experimentation.

Figure 4:
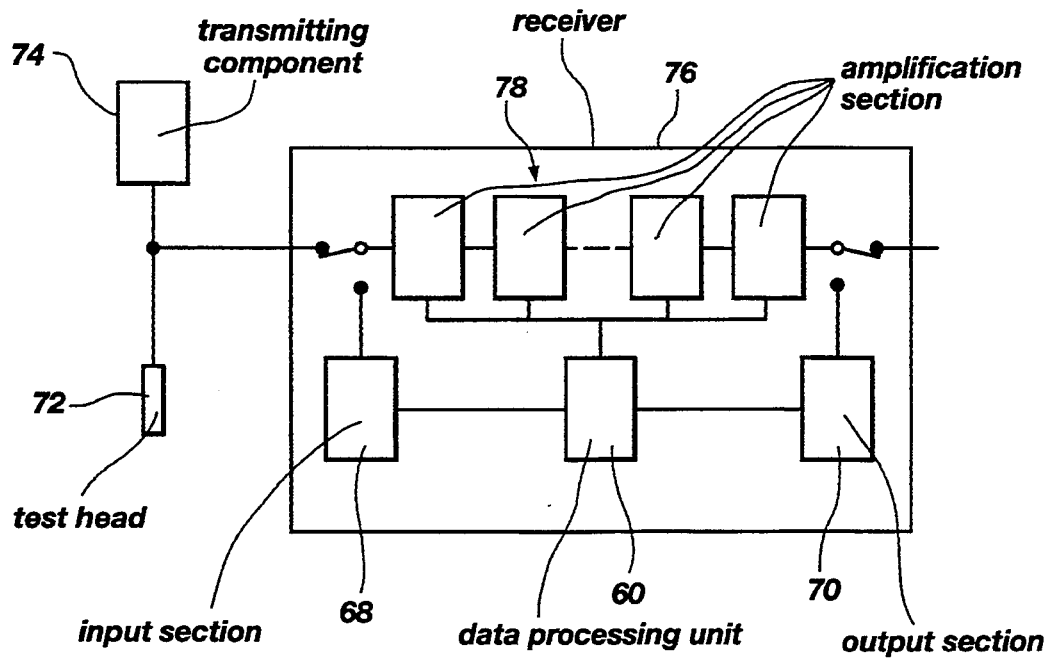
FIG. 4 shows a block circuit diagram for an ultrasonic measuring device.

FIG. 4 shows in the form of a block circuit diagram the ultrasonic measuring device constructed in accord with the invention. A transmitting component 74 delivers impulses to an ultrasound test head 72, and the echoes that this picks up are amplified in the receiver 76 which is characterized by an amplifier 78 that is constructed in accord with the invention.

We claim:

1. An ultrasonic measuring device for non-destructive testing of materials comprising the following in combination:

an ultrasound test head;
   a transmitter;
   a receiver having a broadband logarithmic amplifier, said amplifier having multiple identical amplification stages connected in series:
   each of said amplification stages having two transistorized individual amplifiers, namely a first and a second differential amplifier connected to one another and the transistors of each one interconnected at bases and at collectors; each of the transistors being further connected at emitters through inverse feedback resistors to a constant-current source; and said constant-current source of one of the two differential amplifiers of said amplification stage being connected on one side to a digital analog transformer that provides corrections for calibrating each connected constant-current source.

2. An ultrasound measuring device in accordance with claim 1, wherein each of said amplification stages is equipped with two constant-current sources, of which one is variable.

3. An ultrasonic measuring device in accordance with claim 1, wherein one of the two individual amplifiers of each of said amplification stages is equipped with two constant-current sources, of which one is variable.

4. An ultrasonic measuring device in accordance with claim 1, including a calibration unit, which is composed of an input section that provides input voltages of various levels and an output component that picks up the output voltages that arise for the said input voltages at an exit of said broadband logarithmic amplifier, the calibration unit being connected to a data processing unit.

5. An ultrasonic measuring device in accordance with claim 4, wherein said broadband logarithmic amplifier has an input for implementing an iterative process, in which a nominal constant current I1 is first set for all said amplification stages and n test signals are directed to the broadband logarithmic amplifier, with n being the number of amplification stages; and wherein the output voltages are picked up via the output component, and corrected values for the constant current in the data processing unit are calculated from the deviations from the expected proportional relationship between input voltages and output voltages.

6. An ultrasonic measuring device in accordance with claim 1 wherein the said broadband logarithmic amplifier can be adjusted between linear and logarithmic mode of operation using a switching arrangement (S1, S2) for each of said amplification stages, thereby switching between an amplification V=1, an amplification V=Vo and an amplification with the following characteristic curve:

V=Vo for input voltages Uin≦Uo and V=1 for Uin>Uo.

7. An ultrasonic measuring device in accordance with claim 6, wherein the first differential amplifier has two inverse feedback resistances which are selected in such a way that the amplification of said first differential amplifier is V=1, and that the second differential amplifier has two inverse feedback resistances, which are smaller than those of the first differential amplifier and selected in such a way that a total amplification is V=Vo; and in addition to at least one constant-current source being connected on one side to the digital analog transformer with the presence of two further constant-current sources, the three constant-current sources can be connected via a switching arrangement to the two differential amplifiers, with two of the said three constant current sources providing a current I1/2 while the third of said constant current sources delivers a current I2, thereby providing the capacity to be connected via the switching arrangement to input points on the two differential amplifiers in accordance with the following table:

| switching position | first input point 38 | second input point 44 |
|---|---|---|
| log | I1/2 + I1/2 | I2 |

-continued

| switching position | first input point 38 | second input point 44 |
|---|---|---|
| V = 1 | I1/2 + I1/2 | — |
| V = Vo | I1/2 | I1/2 |

8. An ultrasonic measuring device in accordance with claim 1, wherein the interconnected collectors of said transistors on a left hand side and the interconnected collectors of said transistors on a right side of a differential amplification stage are each connected via a collector resistance to a voltage supply with the value of each said collector resistance equaling the value of the inverse feedback resistances of the first differential amplifier.

9. An ultrasonic measuring device in accordance with claim 6, wherein the said switching arrangement (S1, S2) is composed of electronic switches.

10. An ultrasonic switching device in accordance with claim 4, in which the said switching arrangement (S1, S2) is connected to a data processing unit.

11. An ultrasonic measuring device in accordance with claim 6, wherein the said switching arrangement (S1, S2) is constructed in such a way that, upon switching, electric contact is first made with a new switch contact before the electric connection to an old switch contact is interrupted.

12. An ultrasonic measuring device in accordance with claim 6, wherein a current I1/2 is greater than a current I2, preferably at least three times greater and ideally at least five times greater.

13. An ultrasonic measuring device in accordance with claim 1, wherein the transistors are constructed identically and on a single semiconductor base.

14. An ultrasonic measuring device in accordance with claim 6 wherein in an arrangement incorporating at least three differential amplifiers having said amplification stages arranged in series, the switching arrangements (S1, S2) for each said differential amplifiers are so interconnected that all said differential amplifiers are together in either linear or logarithmic mode of operation, with each of said amplification stages being independent of the others in the linear amplification factor while in the linear mode of operation.

15. An ultrasonic measuring device in accordance with claim 7, characterized by the fact that each said amplification stage has two collector resistances, such that the two collector resistances of each said amplification stage have equal resistance values, such that each of the collector resistances has a resistance value that is the same as the resistance value of one of said two inverse feedback resistances of said first and second differential amplifiers and that said two inverse feedback resistances of said first and second differential amplifiers have the same resistance value.

* * * * *